(12) United States Patent
Darling (10) Patent No.: US 8,501,205 B2
(45) Date of Patent: Aug. 6, 2013

(54) INSECT REPELLENT COMPOSITION

(76) Inventor: Samuel T. Darling, Salt Spring Island (CA)

( * ) Notice: Subject to any disclaimer, the term of this patent is extended or adjusted under 35 U.S.C. 154(b) by 49 days.

(21) Appl. No.: 12/949,431

(22) Filed: Nov. 18, 2010

(65) Prior Publication Data

US 2011/0183017 A1    Jul. 28, 2011

Related U.S. Application Data

(63) Continuation of application No. 11/623,209, filed on Jan. 15, 2007, now Pat. No. 7,846,464.

(60) Provisional application No. 60/766,388, filed on Jan. 16, 2006.

(51) Int. Cl.
*A01N 25/00* (2006.01)
*A01N 65/00* (2009.01)
*A61K 38/00* (2006.01)

(52) U.S. Cl.
USPC ............ 424/405; 424/406; 424/750; 424/725

(58) Field of Classification Search
USPC .......................... 424/750, 405, 725
See application file for complete search history.

(56) References Cited

U.S. PATENT DOCUMENTS

| | | | |
|---|---|---|---|
| 4,053,438 A | 10/1977 | DeSimone | |
| 4,822,614 A | 4/1989 | Rodero | |
| 5,565,208 A | 10/1996 | Vlasblom | |
| 5,698,209 A | 12/1997 | Shono et al. | |
| 5,948,423 A | 9/1999 | Karg | |
| 6,660,288 B1 | 12/2003 | Behan et al. | |
| 2002/0116867 A1 | 8/2002 | Allison et al. | |
| 2003/0096878 A1 | 5/2003 | Harper et al. | |
| 2004/0001870 A1 | 1/2004 | Durand et al. | |
| 2005/0181001 A1 | 8/2005 | Roentsch et al. | |
| 2006/0083763 A1* | 4/2006 | Neale et al. ................... | 424/405 |

FOREIGN PATENT DOCUMENTS

| | | |
|---|---|---|
| WO | WO 02/43489 | 6/2002 |
| WO | WO 02/43656 | 6/2002 |
| WO | WO2005/112632 | 12/2005 |

OTHER PUBLICATIONS

Vanillin pubchem reference (downloaded from the internet on Aug. 17, 2012, created dated Sep. 16, 2004, URL: http://pubchem.ncbi.nlm.nih.gov/summary/summary.cgi?cid=1183.*

Candia J.L, Xanthum Gum, section 4, p. 1-3, Encyclopedia of Bioprocess Technology: Fermentation, Biocatalysis and Bioseparation, Copyright 199 by John Wiley & Sons, Inc. Article onine posting date: Oct. 15, 2002.

Oyedele et al, Phytomedicine, vol. 9, 2002, pp. 259-262.

Kroger, A., Gerhardus, A., Kruger, G., Mancheno, M., and Pesse, K., 1997. "The Contribution of Repellent Soap to Malaria Control". American Journal of Tropical Medicine and Hygiene 56: 580-584.

(Continued)

*Primary Examiner* — Savitha Rao (74) *Attorney, Agent, or Firm* — Baker Botts L.L.P.

(57) ABSTRACT

The present application provides insect repellent compositions that include lemongrass oil and p-menthane-3,8-diol. Vanillin or a vanillin-type component may also be included in the insect repellent composition.

15 Claims, 2 Drawing Sheets treatment and hour after application

OTHER PUBLICATIONS

Rowland, M., Freeman, T., Downey, G., Hadi, A., and Saeed, M., 2004. "DEET mosquito repellent sold through social marketing provides personal protection against all-night mosquito biting and partial coverage of insecticide-treated nets: a case-control study of effectiveness". Tropical Medicine and Inernational Health 9: 343-350.

Worrall, E., Basu, S., and Hanson, K., 2005. "Is malaria a disease of poverty? A review of the literature". Tropical Medicine and International Health 10: 1047-1059.

Barnard, D., Bernier, U., Posey, K., Xue, R., 2002. "Repellency of IR3535, KBR3023, para -methane-3,8-diol, and Deet to Black Salt Marsh Mosquitos (Diptera: Culicidae) in the Everglades National Park". Journal of Medical Entomology 39: 895-899.

Curtis, C.F., Lines, J.D., Ijumba, J., Callaghan, A., Hill, N., and Karimzad, M.A., 1987. "The relative efficacy of repellents against mosquito vectors of disease". Medical and Veterinary Entomology 1: 109-119.

Rutledge, L.C., Gupta, R.K., Mehr, Z.A., Buescher, M.D., and Reifenrath, W.G., 1996. "Evaluation of Controlled-Release Mosquito Repellent Formulations". Journal of the American Mosquito Control Association 13: 39-44.

Schreck, C.E., and Leonhardt, B.A., 1991. "Efficacy Assessment of Quwenling, A Mosquito Repellent From China". Journal of the American Mosquito Control Association 7: 433-436.

Moore, S.J., Lenglet, A., and Hill, N., 2002. "Field Evaluation of Three Plant-Based Insect Repellents Against Malaria Vectors in Vaca Diez Province, The Bolivian Amazon". Journal of the American Mosquito Control Association 18: 107-110.

Trigg, J.K., 1996. "Evaluation of a Eucalyptus-Based Repellent Against Anopheles SPP. In Tanzania". Journal of the American Mosquito Control Association 12: 243-246.

Rowland, M., Downey, G., Rab, A., Freeman, T., Mohammad, N., Rehman, H., Durrani, N., Reyburn, H., Curtis, C., Lines, J., and Fayaz, M., 2004. "DEET mosquito repellent provides personal protection against malaria: a household randomized trial in an Afghan refugee camp in Pakistan". Tropical Medicine and International Health 9: 335-342.

Constantini, C., Badolo, A., Ilbouldo-Sanogo, E., 2004. "Field evaluation of the efficacy and persistence of insect repellents DEET, IR3535, and KBR 3023 against *Anopheles gambiae* complex and other Afrotropical vector mosquitoes". Transactions of the Royal Society of Tropical Medicine and Hygiene 98: 644-652.

Harris, A.F., Matias-Améz, A., Hill, N., 2006. "Biting time of *Anopheles darlingi* in the Bolivian Amazon and implications for control of malaria". Transactions of the Royal Society of Tropical Medicine and Hygiene 100: 45-47.

Korenromp, E., Miller, J., Nahlen, B., Wardlaw, T., Young, M., 2005. World Malaria Report 2005. World Health Organization and UNICEF.

Malaria Centre Report 2004-2005 (eds. Whitty, C. & Aldous, C.). Bucks: London School of Tropical Medicine and Hygiene, 2005.

Notice of Allowance issued Sep. 7, 2010 on U.S. Appl. No. 11/623,209.

Amendment after final filed Sep. 7, 2010 on U.S. Appl. No. 11/623,209.

RCE/amendment filed Jun. 16, 2010 on U.S. Appl. No. 11/623,209.

Final rejection issued Feb. 19, 2010 on U.S. Appl. No. 11/623,209.

Amendment filed Dec. 2, 2009 on U.S. Appl. No. 11/623,209.

Amendment filed Oct. 15, 2009 on U.S. Appl. No. 11/623,209.

Non-final rejection issued Jul. 17, 2009 on U.S. Appl. No. 11/623,209.

Amendment filed May 4, 2009 on U.S. Appl. No. 11/623,209.

Final rejection issued Dec. 2, 2008 on U.S. Appl. No. 11/623,209.

Amendment filed Jul. 24, 2008 on U.S. Appl. No. 11/623,209.

Non-final rejection issued Mar. 28, 2008 on U.S. Appl. No. 11/623,209.

Extended European Search Report for EP Application No. 07710142.6, dated Apr. 3, 2013.

Barnard, et al., "Laboratory Evaluation of Mosquito Repellents Against Aedes albopictus, Culex nigripalpus, and Ochlerotatus triseriatus (Diptera: Culicidae)", *Journal of Medical Entomolgy, Entomological Society of America,* 41(4):726-730 (2004).

Trongtokit, et al., "Efficacy of Repellent Products Against Caged and Free Flying Anopheles Stephensi Mosquitoes", *Souteast Asian J. Trop. Med. Public Health*, pp. 1423-1431 (2005) Retrieved from the internet: URL:http://imsear.hellis.org/bitstream/123456789/31300/2/1423.pdf. [Retrieved on Mar. 15, 2013 ].

Tawatsin, et al., "Repellency of Volatile Oils from Plants Against Three Mosquito Vectors", *Journal of Vector Ecology,* 26(1):76-82 (2001).

Ansari, et al., "Relative Efficacy of Various Oils in Repelling Mosquitoes", *Database Medline, US National Library of Medicine, Indian Journal of Malariology.* 32(3):104-111 (1995) (XP002693996).

* cited by examiner

INSECT REPELLENT COMPOSITION

CROSS REFERENCE TO RELATED APPLICATION

This application is a continuation of U.S. application Ser. No. 11/623,209, filed Jan. 15, 2007, issued as U.S. Pat. No. 7,846,464, which claims the benefit of priority under 35 U.S.C. §119(e) of U.S. Provisional Application No. 60/766,388, filed Jan. 16, 2006. Each of these applications are hereby incorporated by reference in their entirety.

FIELD OF THE INVENTION

The present application relates to insect repellent compositions.

BACKGROUND OF THE INVENTION

In many areas of the world, insect bites are not just a nuisance; they are a serious danger to health. Most notably, such bites may result in the transmission of life threatening and debilitating diseases such as malaria, dengue fever, yellow fever, or the West Nile virus. Hence, there remains an ongoing need to improve the currently available insecticides.

Recent modeling work, based on population and malaria infection risk data in 2002[1], indicates that 61%—i.e. ca. 656 million cases—occur annually in the WHO Regions of the Americas, Southeast Asia and the Western Pacific. In 2005, the WHO reported that 41% of clinical malaria cases occur outside of Africa[2], an increase in comparison to their 2001 estimate of 13.6%[3]. This growing awareness of the malaria problem beyond Africa should encourage the diversification of global research into malaria vector control—a matter of great importance, as mosquito vectors in these regions generally exhibit behavior that makes them less susceptible to control measures shown to be effective in sub-Saharan Africa, including insecticide treated bednets (ITNs) and indoor residual spraying (IRS).

These behaviors include tendencies of 1) outdoor resting, e.g. Anopheles darlingi[4] and An. dirus[5]; 2) outdoor feeding, e.g. An. minimus,[5] An. darlingi[4], and An. sinensis[5]; and 3) significant feeding activity during early evening, e.g. An. albimanus,[6] An. nunetzovari[6], An. farauti No. 2[7], and An. darlingi.[8] The introduction of ITNs in several areas also appears to have caused behavioral shifts among malaria vectors, with outdoor and early evening feeding becoming more frequent in areas where those control tools are in place[9,10]. A feasibility study for implementing ITNs in four Latin America countries showed that 25% of An. albimanus in Nicaragua, 28% of An. punctimacula in Ecuador, 57% of An. albitnanus in Peru, and 30% of An. nunetzavari, also in Peru, fed before 9 p.m., when people are still active and often still outdoors.[11] More recently, a case-control study in Colombia[12] showed that ITNs provided only a 50% reduction in malaria, and this was attributed by the authors to mosquito's biting when people were not sleeping beneath the nets.

In such transmission conditions, ITNs may be usefully supplemented by insect repellents [13,14]. A recent household randomized trial in Pakistan[15] has confirmed that the widespread provision of repellents—in this case, a repellent soap incorporating DEET and permethrin—can significantly reduce the risk of malaria by >50%. Furthermore, a clinical trial in the Bolivian Amazon,[16] with a 30% p-menthane 3,8-diol (PMD) repellent showed an 80% reduction in P. vivax, among those using repellent and ITNs, compared to an ITN only group.

Much malaria and arbovirus transmission in the Americas is related to working practices, and the movement of non-immune people into malaria endemic areas in search of work in the forests (mining, logging etc).[17] Young workers suffer the greatest hardship from this disease, which creates severe economic pressures for the whole family through loss of earnings,[18] labor replacement, and treatment costs.[19] For the poorest families in Latin America, these indirect costs may correspond to between 12 and 20% of annual household income[19,20]. With this in mind, a low cost repellent was developed that contains natural ingredients that are aromatically familiar to users and may eventually be sourced locally.

It is known that there are substances, including natural isolates, which can provide an insect repellency effect. Repellent substances are known to provide this effect when applied to a surface (e.g. human skin or hard surfaces) usually with an appropriate delivery vehicle (e.g. aerosol, lotion, spray, gel, etc.) and are commonly referred to as "insect or bug repellents".

Examples of repellent materials which impart a repellency effect include, but are not limited to, materials such as N,N-diethyl m-toluamide (hereafter referred to as DEET), p-menthane-3,8-diol (commonly referred to as Coolact® 38D, registered trademark of Takasago International Corp.), permethrin, allethrin, piperonyl butoxide, lemongrass oil, citronella oil, eucalyptus oil, camphor, geranium oil, ethyl hexanediol, ethyl butylacetylaminopropionate, and hydroxyethyl-isobutyl-piperidine.

In a commercial repellent formulation, the repellent agents are typically added as a single active ingredient to produce the desired effect. It should be noted that there is at least two examples of a combination of two repellent materials being used in a composition. For example, U.S. Pat. No. 5,698,209 discloses a composition containing a monoterpenediol selected from carane-3,4-diol and p-menthane-3,8-diol (Coolact® 38D) and a pyrethroid compound selected from phenothrin and permethrin as active ingredients. The composition purportedly exhibits a high arthropod repellency for a long period of time. Also, Japanese Publication No. JP 3-133906 discloses a combination of p-menthane-3,8-diol and N,N-diethyl-m-toluamide (DEET). It should also be noted that there are other examples in the patent literature wherein an essential oil containing composition is claimed to possess repellent properties (see e.g., U.S. Published Application No. 2005/0112164 A1).

The active ingredient in a majority of commercial insect repellents is DEET which has been shown to be effective against a wide variety of biting insects. However, the use of DEET has several drawbacks including potential health risks and concerns, especially to children, since it is absorbed through human skin. In addition, the odor of DEBT is considered by many to be "chemical" and unpleasant and it can sting when applied to the skin. Hence, a suitable consumer friendly repellent formulation is needed.

BRIEF DESCRIPTION OF THE DRAWINGS

In FIG. 1, C15 is 15% PMD (derived from Corymbia citriodora oil; Chemian Technology Ltd) with Lemon Grass oil (Cymbopongon ciratus; the Essential Oil Company Ltd.), filler and fixative. T15 is 15% PMD (derived from Pine oil; Takasago International Corporation) with LG oil, filler and fixative. T20 is 20% PMD (Takasago International Corporation) with LG oil, filler and fixative. % Protection is 100−((mosquito landings on treatment÷mosquito landings on control)×100).

In FIG. 2, PMD/LG is a modified repellent formulation of 16% PMD (Takasago International Corporation), with LG oil (Berje), filler and fixative. % Protection is 100−((mosquito landings on treatment÷mosquito landings on control) ×100.

SUMMARY OF THE INVENTION

The present application is based on a surprising discovery which alleviates the above mentioned product limitations. The discovery encompasses the use of two repellent materials, in combination, in a unique formulation to afford a product with added benefit and superior efficacy that can be made available to individuals in developing nations at an affordable price. It has been discovered that the novel combination of p-menthane-3,8-diol and lemongrass oil affords an effective insect repellent with superior efficacy and attributes to either of the individual repellents or any other commercial product. It has also been found that the inclusion of vanillin or a vanillin-like component is also helpful to repel insects. Formulations containing lemongrass oil and p-menthane-3,8 diol been shown to effectively repel the *Anopheles darlingi* and *Anopheles albimanus* mosquitoes which vector malaria, the *Aedes aegypti* mosquito which vectors dengue fever and yellow fever.

DETAILED DESCRIPTION

Definitions

As used herein, the term "insecticide" or "repellent" refers to any substance or mixture of substances used to kill or control or repel any insect. Herein, the insecticide or repellent as defined has a preferred use to kill or control or repel flying insects (e.g. mosquitoes). However, it is anticipated that the insecticide formulation described will also be effective against mites, ticks (Lyme disease), and numerous other insects.

As used herein, the abbreviation "PMD" refers to p-menthane-3,8 diol.

As used herein, the abbreviation "LG oil" refers to lemongrass oil.

As used herein, the term "fixative" refers to compounds that extend the life of repellents by slowing the evaporation of volatile repellent actives (e.g. PMD and lemongrass oil). An example of a preferred fixative is vanillin.

Lemongrass Oil

Lemongrass oil is a distillate of *Cymbopogon citratus* leaves. It is commercially available from various sources, including from The Essential Oil Company Ltd., Worting House, Church Lane, Basingstoke, Hants., United Kingdom, Berje Inc., Bloomfield, N.J. and Polarome, Jersey City, N.J. Lemongrass oil may be obtained for about $12-25 per kilogram.

Lemongrass oil may be less expensive than most active ingredients used in insect repellents. Surprisingly, lemongrass oil, when combined with p-menthane-3,8 diol and/or vanillin, provides an insect repellent that is as powerful, or more powerful than insect repellents containing much larger amounts of more expensive actives. Accordingly, inclusion of lemongrass oil in insect repellents of the present application provide an insect repellent with increased efficacy that is affordable to individuals living in insect-prone areas, including developing nations in the Central and South America.

p-methane-3,8-diol

P-menthane-3,8-diol (PMD) has the following structure:

PMD is commercially available (as a mixture of (+)-cis & (−)-trans p-Menthane-3,8-diol) under the trademark Coolact® 38D from Takasago Int'l Corporation (U.S.A.), Rockleigh, N.J.

P-menthane-3,8-diol may also be derived by acid modification of the oil of *Corymbia citriodora* (the lemon eucalyptus), which is grown commercially (e.g. commercially grown in Brazil and other Latin American countries). Citriodiol, which is a product of the extract of the leaves of *Corymbia citriodora*, contains about 60% p-menthane-3,8-diol. See Annals of Tropical Medicine & Parasitology (Ann. trop. med. parasitol.) 2005, vol. 99, no7, pp. 695-715, which is hereby incorporated by reference.

Coolact® 38D is a preferred source of p-menthane-3,8-diol since it is a purer form, as compared to PMD derived from *Corymbia citriodora*.

Vanillin and Related Compounds

Insect repellent compositions of the present application may also contain vanillin or a vanillin-like component represented by the formula:

wherein A is a hydrogen, hydroxy, or an unsubstituted, branched or straight-chained $C_1$-$C_4$ alkyl carboxy group, B is a hydroxy or an unsubstituted, branched or straight-chained $C_1$-$C_4$ alkyoxy group, D is a bond or a unsubstituted, branched or straight-chained $C_1$-$C_4$ alkyl group optionally interrupted by an oxygen, E is a hydrogen or an unsubstituted, branched or straight-chained $C_1$-$C_4$ alkyl group, and F is hydrogen or hydroxy. Vanillin-like components that may be used in repellent compositions of the present invention include, but are not limited to, vanillin acetate, vanillin isobutyrate, and ortho-vanillin. In a preferred embodiment, insect repellents of the present invention contain vanillin, which is commercially available from Rhodia Inc. (Cranbury, N.J.) and has the following structure:

While not being bound by any particular theory, it is believed that the vanillin, or vanillin-like component reacts with lemongrass oil, PMD, alkylene glycols or ethanol found in the insect repellent to form acetal compounds to increase the effectiveness of the insect repellent. Over time, the acetals are believed to hydrolyze back to the starting material, (e.g. PMD). Exemplary reaction schemes are shown below:

*trans configuration of p-menthane-3,8 diol is shown above. Generally, the p-menthane-3,8 diol may be present in both cis and trans forms.

Additional Components

Additional components may be added to the insect repellents of the present application, such as fragrances, solvents, diluents and fixatives. Non-limiting examples of such materials are disclosed in U.S. Pat. No. 6,660,288 which is hereby incorporated by reference, and include: Aldehyde C11 (Undecylenic Aldehyde); Aldehyde iso C11 (GIV); Allspice oil; Allyl cyclohexyl propionate; Amyl salicylate; Amylcinnamic aldehyde; Anethole; Anisic alcohol; Anisic aldehyde; Applinal (Q); Bay oil; Benzyl acetate; Benzyl benzoate; Benzyl cinnamate; Benzyl propionate; Benzyl salicylate; Bourgeonal (Q); Brahmanol; Camphor powder synthetic; Cedarwood Virginian; Cedrenol; Cedryl acetate; Celestolide (IFF); Cineole; Cinnamic alcohol; cinnamic aldehyde; Cinnamon Leaf Oil: Cinnamyl acetate; cis-3-Hexenol; Citral; Citronella oil; Citronellal; Citronellol; Citronellyl acetate; Citronellyl oxyacetaldehyde; Clove oil; Coriander oil; Coumarin; Cuminic aldehyde; Cyclamen aldehyde; Decanal; 9-Decenol; Dibenzyl ether; Dibutyl phthalate; Diethyl Phthalate; Dihydromyrcenol; Dimethyl anthranilate; Dimethyl phthalate; Dimycretol (IFF); diphenylmethane; Diphenyl oxide; Dimethyl benzyl carbinyl acetate; Dodecanol; Dodecanal; Elemi oil; Ethyl methyl phenyl glycidate; Ethyl cinnamate; Ethyl safranate (Q); ethyl vanillin; Eugenol; Evergreen oils (Pine oils etc.); gamma-Nonalactone; gamma-undecalactone; Geraniol; Geranium bourbon; Geranyl acetate; Geranyl formate; Gum Benzoin; Heliotropin; Hercolyn D (HER); Hexyl benzoate; Hexylcinnamic aldehyde; Hydratropic aldehyde dimethyl acetal; Hydroxycitronellal; Hydroxycitronellal dimethyl acetal; Indole; iso Bomyl acetate; Isopropyl myristate; Iso-cyclocitral (GIV, IFF); Jasmacyclene; Jasmin oil; Lavandin Abrialis; Lavender oil; Lilial (GIV); Linalol; Linalyl acetate; Menthol Laevo; Methyl anthranilate; Methyl cedryl ketone; Methyl dihydrojasmonate; Methyl ionone; Methyl myristate; Methyl naphthyl ketone; Methyl salicylate; Moss treemoss; Musk ketone; Nerol; Nerolin Bromelia; Neryl acetate; Nonanal; Oakmoss absolute; Octanol Olibanum resionoid; para-Cresyl phenylacetate; para-Methoxyacet6-phenone; Patchouli oil; Peppermint oil; Petitgrain oil; 2-Phenoxyethanol; Phenoxyethyl iso butyrate; Phenylethylacetate; Phenyethyl alcohol; Phenylethyl butyrate; Phenylethyl phenylacetate; Pimento oil; Pinene, alpha; Para-tert. butyl-cyclohexyl acetate; Resinoid Benzoin Siam; Rose oil; Rosemary oil; Sandalwood oil; terpineol; Tetrahydrolinalol; Tetrahydromuguol (IFF); Thyme Red; Undecanal; Vanillin; Verbena oil; Vetyvert Bourbon; Yara and Ylang ylang, acidic mucopolysaccharides and their salts, Aesculus hipocastanum, aloe barbadenisis Mil (Aloe Vera Linne), .alpha.-hydroxycarboxylic acids, .alpha.-ketocarboxylic acids, amide derivatives, amino acids, amphiphilic cyclodextrin derivatives, .beta.-sitosterol, carboxy vinyl polymer water soluble salts, carboxymethyl cellulose, carrageenan, chitin, chitosan, cholesterol, cholesterol fatty acid ester, collagen, dicarboxylic acid monostearyl esters, di-fatty acid glycerol esters, digalactosyl diglyceride, ersterol, ethanol, extract of *Swertia japonica* Makino, fatty acids, fatty acid citrate esters, fatty alcohols, ginseng extract, glucose esters of higher fatty acids, guar gum, gum arabic, Hamamelidaceae (Hamamelis Virginiana Witch hazel), hyaluronic acid, hydrochyloesterol, hydroxybenzoic acids, isomaltose, isopropyl alcohol, lactose, lanosterol, lipids extracted from the biomass of microorganisms, yeasts, moulds and bacteria, liposomes, locust bean gum, low molecular acidic mucopolysaccharides and their salts, low molecular weight humectant components, maltose, mineral oils, mineral powders, mono cis alkenoic acid, mucopolysaccharides, mycosterol, N-acyl lysines, N-isostearyl lysine, N-lauroyl lysine, N-myristyl lysine, N-palmitoyl lysine, N-stearoyl lysine, natrium type bentonite, natural or synthetic aminoacid with protein or peptide bonds, NMF ingredients, nonvolatile silicones, oil agents, oil matter, oligosaccharides, organic acids, pantothenic acid and its derivatives, petroleum jelly, phosphatidyl ethanolamine, phosphatidylcholine, phospholipids, polysaccharides, polyvinyl alcohol, polypeptides, proteins, raffinose, saponins, sodium hyaluronate, sources of linoleic acid, sterols, sterol esters, stigmasterol, sucrose, sugar esters of higher fatty acids, sulphatide, sunscreens, surfactants, talc, thymosterol, tocopherol, mono-, di- or tri-glycerides, vitamins and analogues, vitamin E and/or its ester compounds, volatile silicone fluids, water-soluble moisture-retaining agents, water-soluble polymers and waxes.

Insect Repellent Compositions

The use level of the repellent composition, i.e. the amount of the composition containing lemongrass oil, and p-menthane-3,8 diol and, when present in the insect repellent composition, vanillin, may vary from about 1.0 wt % to about 100.0 wt % of the finished product, depending on the specific product and application. In a preferred embodiment the use level of the repellent composition ranges from about 5% to about 50%, more preferably from about 10% to about 35%. In one embodiment, the use level of the repellent composition is about 20-30%.

The weight ratio of p-menthane-3,8-diol (e.g. Coolact® 38D) to lemongrass oil (PMD:LG oil) in the repellent combination can vary from about 1:99 to about 99:1, more preferably from about 10:1 or 7.5:1 to about 5:1 or 2:1. It is possible that the different combinations of the repellent materials could result in higher or lower use levels depending on application.

The weight ratio of vanillin (or a related vanillin-type compound) to lemongrass oil (vanillin:LG oil) ranges from about 3:1 to about 0.25:1, more preferably from about 2:1 to 0.5:1 (e.g. 1:1). In a preferred embodiment, vanillin is present in the insect repellent composition in the amount of about 5 to 10 wt %.

In one embodiment, the weight percentage of p-menthane-3,8 diol is less than about 30 wt %, based on the total weight of the insect repellent composition. In other embodiments, the weight percentage of p-menthane-3,8 diol is less than about 25 wt %, or 24 wt %, or 23 wt %, or 22 wt % or 21 wt %, or 20 wt %, or 19 wt %, or 18 wt %, or 17 wt %, or 16 wt %, or 15 wt % or 14 wt %, or 13 wt %, or 12 wt %, or 11 wt %, or 10 wt %, based on the total weight of the insect repellent composition.

EXAMPLES

The following examples illustrate the invention without limitation.

Example 1

Two Phase Formulation

Insect Repellent Lotion

| INGREDIENTS | PERCENT (wt %) |
| --- | --- |
| Mineral oil | 39.0% |
| Ethanol | 26.0% |
| p-menthane-3,8-diol | 16.0% |
| dipropylene glycol | 8.5% |
| lemon grass oil | 5.0% |
| Vanillin | 5.5% |

The use level of the repellent combination in the lotion formulation for the following example was 26.5 wt %.

Vanillin was added to the formulation last. Prior to adding the vanillin, heat is applied to the PMD so that it has a viscosity suitable for introduction to the admixture. The resulting composition has a non-greasy feel, and has the viscosity of a light oil.

A suitable volume of the above formulation to be applied to a the skin of the user is about 2 ml per 1000 cm$^2$ of skin. The formulation should be clear two-phase formulation and can be then filled into suitable plastic containers (PET preferred) and is to be shaken vigorously before applied to a user.

Example 2

One Phase Formulation

The following ingredients were combined as described below:

| Ingredient | Supplier | Percentage (wt %) |
| --- | --- | --- |
| Mineral Oil | ISP | 30.00 |
| Isoparaffinic Hydrocarbon | ExxonMobil$^A$ | 8.00 |
| p-menthane-3,8-diol | Takasago | 16.00 |
| Isononyl acetate | IFF | 35.50 |
| Lemongrass oil | Berje Guatamala | 5.00 |
| Vanillin | Rhodia | 5.50 |

$^A$Available under the trademark Isopar L

Procedure
1. In a suitable vessel, mix the Mineral oil, Isopar L and the p-Menthane-3,8-diol. The PMD may need to be heated slightly (about 100° F.) so that it is liquid. This solution should be clear.
2. In a separate vessel, mix the Isononyl Acetate, Lemongrass Oil and Vanillin until the Vanillin is completely dissolved and the solution is clear. Very slight heat will quicken this (100° F.).
3. With agitation, add part 2 to part 1 and mix until uniform. The formulation should be clear and can be then filled into suitable plastic containers (PET preferred).

Example 3

Gel Formulation

The following ingredients were added sequentially:

| 1) WATER | 42.95% |
| --- | --- |
| 2) MINERAL OIL | 30.00% |
| 3) PMD | 16.0% |
| 4) XANTHAN GUM | 0.55% |
| 5) VANILLIN | 5.5% |
| 6) LEMONGRASS OIL | 5.0% |

The admixture was mixed until a viscous gel was formed. Viscosity of the gel may be adjusted based on the amount of the gelling agent (xanthan gum).

Example 4

Evaluation of the Efficacy of the Formulation of Example 1

Study A—Guatemala Study. The following repellent formulations (% by weight) were used: (1) $C_{15}$: repellent containing the amounts of ingredients described in Example 1—the PMD obtained from acid modification of *Coryinbia citriodora* oil, CAS: 42822-86-6, purchased from Chemian Technology Ltd under the trademark Citriodiol®; (2)115: repellent containing the amounts of ingredients described in Example 1—the PMD obtained from Coolact® 38D; (3) T20: containing 20 wt % PMD instead of 15%, obtained from Coolact® 38D; (4) positive control: 15% DEET (N,N-diethyl-meta-toluamide, CAS 134-62-3; Sigma-Aldrich Co.) in ethanol; (5) negative control: mixture of 20% mineral oil and ethanol.

Study B—Peru Study. Repellent formulations (% by weight) were used: (1) "PMD+LG" containing about 16% PMD as indicated in Example 1—PMD obtained from Coolact® 38D; (2) positive control: 20% DEET (Sigma Aldridge) in ethanol (Sigma-Aldrich Co.); (3) negative control: 20% mineral oil (ExxonMobil Corporation) in ethanol.

Study A and B, Both studies were controlled double blind, human-landing catch design. All solutions were placed in unmarked containers labeled by code. On any one night, human volunteers had both lower legs treated with either one of the PMD/LG candidate repellents or a positive or negative control at a rate of 0.002 ml/cm$^2$ between the ankle and the knee. Volunteers' leg length and circumference were measured to calculate surface area and the correct dose of treatment was measured using a micropipette, and applied using a latex glove to minimize absorption of material onto the hand of the volunteer. During the human-landing catches, the volunteers wore shorts to the knee, work boots, and a loose bug jacket (ProBuy) to ensure that blood-seeking mosquitoes had access only to their lower legs. In addition, to minimize variation in their head space kairomones[27,28], after midday the volunteers did not smoke, consume alcohol, or wash using soap.

The designated locations within the field sites were 10 m from each other and a minimum of 20 m from alternate sources of kairomones such as houses and livestock. As insect repellents act over a distance of less than a meter, and the maximum distance of host attraction of a single human to mosquitoes is 10 m,[29] the design eliminates any "relativity effect" where insects choose between two hosts simultaneously. Mosquitoes were collected from the lower legs of the volunteers once they had settled—without the need to wait for biting—by using a mouth aspirator, flashlight, and a collection vessel. Collection vessels were changed each hour to provide hourly measures of repellency. Umbrellas were also provided, to protect the volunteers from any rain showers that might wash away their repellent.

All volunteers were experienced at conducting man-landing catches. A form outlining procedure was given to the volunteers to ensure that they had full understanding of the potential risks of a study of this kind. In addition, each was given chloroquine (Guatemala) or Mefloquine (Peru) prophylaxis in accordance with WHO guidelines.[30] Full ethical clearance was obtained from Universidad del Valle, Guatemala (Study A); and from London School of Hygiene and Tropical Medicine Ethics Board and Instituto Nacional de Salud, Peru (Study B).

Study A. The three repellents and two controls were applied to the five volunteers at 1430 hrs, and man-landing catches were performed at the field site for one hour before and after sunset (1730-1930 hrs), when the evening mosquito biting is at its peak as shown by preliminary man-landing catches. The times chosen allowed an assessment of the protection afforded by the repellent over 5 hours while exposing volunteers to bites for only 2 hours. This helped minimize exposure and risk to the collectors. The study was a balanced 5×5 Latin-square design that required each volunteer to test each treatment five times throughout the study over a period of twenty-five nights. Every evening, each individual was allocated one of five treatments, and sat in one of five allocated positions. Consequently, the volunteers changed position every five days.

Study B. The repellent and two controls were applied at 1600 hrs, and man-landing collections were performed at the field, between 1800 and 2200 hours, as this is the time of peak *An. darlingi* activity in the area (Chan, A. unpublished data). The times chosen allowed an assessment of the protection afforded by the repellent over to be made of relative protection of the samples for a period of 6 hours while exposing volunteers to bites for only 4 hours. This helped minimize exposure and risk to the collectors. The volunteers took a 15-minute break between 2000 hrs and 2015 hrs. The study was a 3×3 balanced Latin-square design performed using three volunteers over nine nights, with volunteers changing positions every third night. Due to unforeseen circumstances, one of the volunteers was replaced after 4 nights, and this was factored into the statistical analysis.

Mosquitoes were maintained overnight and killed by cooling prior to identification the following morning. Data were normalized using natural log (x÷1) and analyzed with General Linear Model (GLM) using Minitab 11.0 for Windows. Further testing of individual variables was performed using Kruskal Wallis, as data could not be sufficiently normalized to use one-way Analysis of Variance (ANOVA) due to low collection numbers on repellent-treated individuals.

Results

Study A—Guatemala Study.

In 25 nights, 6140 mosquitoes were captured comprising 55.6% Psorophora varipes (Coquillett) and 24.8% *Aedes Ochlerotatus taeniorhynchus* (Say). The average number of mosquito landings on the negative control was 10$^8$ per person/hour and there was no significant difference in hourly numbers of landings in this treatment (H=1.22, d.f.=3 p=0.637). There was no significant difference in hourly landings when data for repellents were analyzed separately (H=0.84, d.f.=1, p=0.360), which indicates that repellent protection did not significantly wane over the course of the test.

Each of the four repellents provided excellent protection from host-seeking mosquitoes, and the PMD/LG repellents provided >96% protection up to five hours after application, with T15 and T20 providing 99% protection. DEET (15%) provided 91% (Table 1). GLM analysis showed that there was a significant difference between the four repellents and the negative control, and between DEET and the three PMD based repellents; although there was no significant difference between the three PMD/LG repellents (d.f=4, F=110.02. p<0.0001) (Table 1). Sources of error in the experimental design were also investigated. There was no significant difference between the collection position within the field site (d.f.=4, F=1.95, p=0.115), although individuals varied in their attractiveness to mosquitoes/collection ability in the GLM (d.f.=4, F=6.17, p<0.0001), but individual variation was no longer significant when analysed separately (H=6.99, df=4, p=0.137). There was a significant interaction between individual and treatment (d.f.=16, F=3.08, p=0.001), but when data for each individual treatment were analysed separately, the only remaining significant interaction was between individual and 15% DEET (d.f.=4, F=4.82, p=0.007) and the PMD-based repellents performed equally well on all five volunteers.

Study B—Peru Study

In nine nights, 2358 mosquitoes were captured, of which 86% were *Anopheles darlingi*. The average number of *An. darlingi* landings on the negative control was 46.27 per person/hour. There was no significant difference in the hourly number of mosquitoes captured from the control (d.f.=3, F=1.18, p=0.333), or repellent treated individuals (H=1.90, d.f.=3, p=0.594), which indicates that the repellents' efficacy did not significantly decline during the four hours of the test.

The PMD/LG repellent ("PMD+LG") significantly outperformed DEET, providing an average of 95% protection 6 hours after application (d.f.=2, F=156.65, p<0.0001) (Table 2). In contrast, 20% DEET provided an average of 62% protection over the duration of the trial. Sources of bias were investigated and there was no difference in the number of mosquitoes captured in the three positions within the field (p=0.972). However, there was significant interaction between tester and repellent (d.f.=6, F=4.85, p<0.0001). When data were analysed separately there was a significant difference between individuals when wearing the negative control (d.f.=3,F=4.51, p=0.010) and wearing repellent "PMD+LG" (H=17.94, d.f.=3, p<0.0001), although DEET protected each individual equally (H=6.85, d.f.=3, p=0.077).

TABLE 1

Efficacy of four repellent formulations tested four and five hours after application during Study A in Guatemala. Figures represent numbers of mosquitoes landing on volunteers' lower legs.

| Treatment | | Hours post application | | | |
|---|---|---|---|---|---|
| | | 4 | 5 | Mean | 95% C.I. |
| Filler mix control | AM | 115.52 | 100.48 | 108.00 | 39.64-82.27 |
| | WM | 79.83 | 66.64 | 56.82$^a$ | |
| | % P | — | — | — | |
| C15 | AM | 1.28 | 5.73 | 3.36 | 0.59-1.86 |
| | WM | 0.64 | 1.40 | 1.05$^b$ | |
| | % P | 94.52 | 94.30 | 96.88 | |
| T15 | AM | 1.36 | 1.44 | 1.40 | 0.64-1.36 |
| | WM | 0.79 | 0.72 | 0.93$^b$ | |
| | % P | 98.82 | 98.57 | 98.75 | |
| T20 | AM | 0.84 | 1.84 | 1.34 | 0.49-1.12 |
| | WM | 0.43 | 0.77 | 0.74$^b$ | |
| | % P | 99.27 | 98.17 | 98.75 | |
| 15% DEET | AM | 6.33 | 12.21 | 9.27 | 2.08-6.29 |
| | WM | 3.63 | 4.87 | 3.60$^c$ | |
| | % P | 94.52 | 87.85 | 91.42 | |

Figure 1:
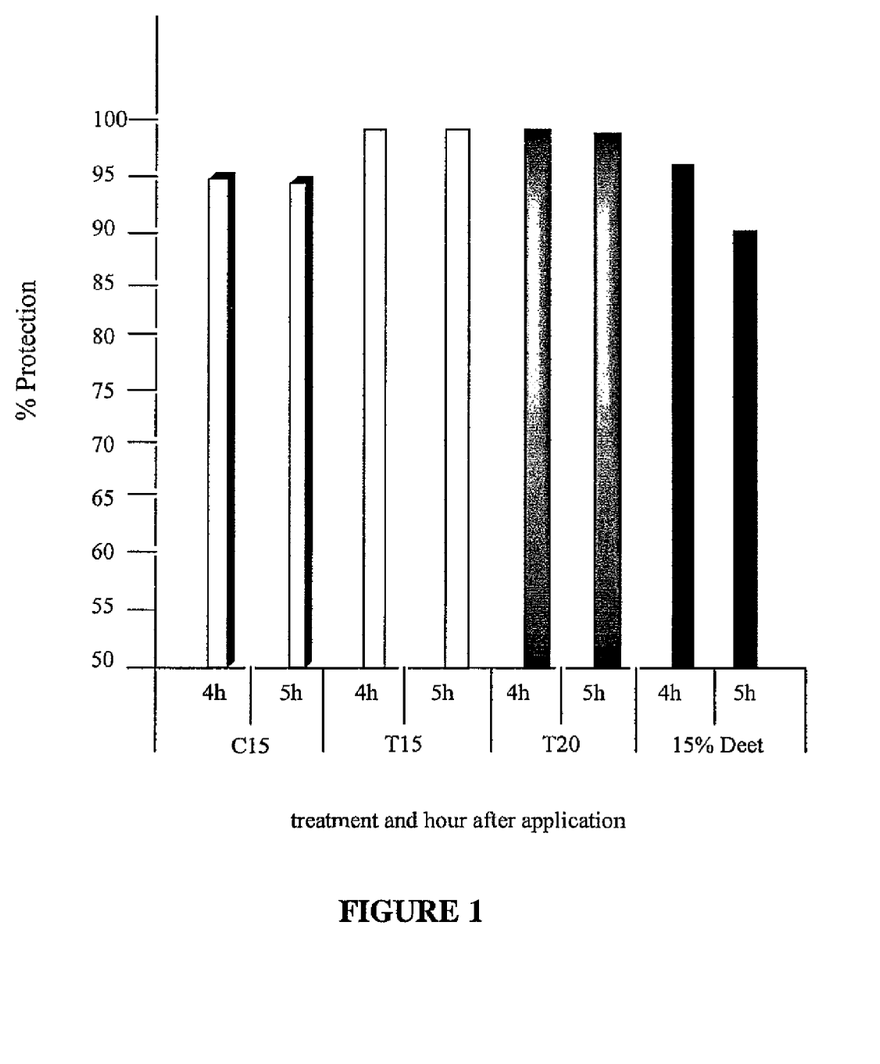
FIG. 1 shows the percentage protection of formulations of the present application, as compared to a control formulation of 15% DEET.
Figure 2:
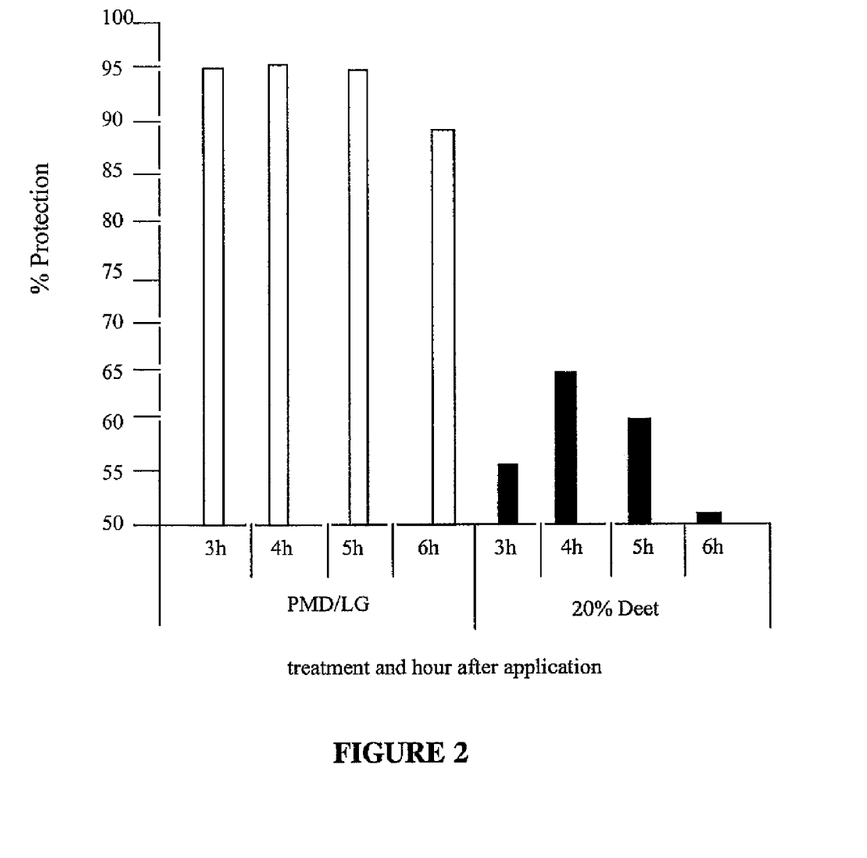
FIG. 2 shows the percentage protection of a formulation of the present application, as compared to a control formulation of 20% DEET.

AM = arithmetic mean mosquito landings/hour
WM = William's mean mosquito landings/hour. Means followed by the same latter are not significantly different.
% P = Percentage protection i.e. 100 − ((mosquito landings on treatment ÷ mosquito landings on control) × 100)
% Protection or the formulations tested in Study A is also shown in FIG. 1.
% Protection against Anophelus darlingi for the formulations tested in Study B are also shown in FIG. 2.

species, with greater than expected longevity for a 15% PMD formulation. Also, in these trials the PMD-based repellents showed greater efficacy than corresponding doses of DEET, whereas several peer-reviewed field studies had shown PMD-only formulations to have similar,[21] or lower,[31] longevity compared to DEET at a corresponding dose. During a 2001 Bolivian field trial against *An. darlingi*, where the biting pressure was 75 mosquito landings per human-hour, a repellent containing 30% PMD provided 97% protection, and 15% DEET provided 85% protection for 4 hours after application.[22] However, in the current Study A, the repellent containing half that concentration of PMD (T15) provided 99% protection for 5 hours after application with a biting pressure of 108 mosquitoes per man hour compared to 91% for 15% DEET. In Study B, a repellent with 16% PMD ("PMD+LG") provided 95% protection for 6 hours after application compared to 62% for 20% DEBT.

It may be inferred from this that the addition of fixatives to the repellents tested in Guatemala and Peru slowed the release of repellent volatiles, thereby extending the repellents duration. It should be emphasized that PMD is the most costly ingredient in the repellent, and the savings realized by a reduction in PMD content from 30% to 15% are substantial. Data from Population Services International (PSI) calculated the daily cost for a 30% PMD-based repellent to be US $0.16 per person per day[32] (in 2001 dollars). Since most of the other ingredients in the PMD/LG repellent are relatively low-cost when purchased in volume, the opportunity to provide an affordable disease prevention tool has been significantly enhanced. There is strong evidence that those of lower socio-economic status are less likely to purchase those forms of personal protection that are relatively more expensive but effective, such as ITNs and repellents, and more likely to rely upon less effective traditional methods of personal protection, such as smoke.[33] Clearly, making the repellent available at the lowest cost possible will enhance user compliance.[34]

The potential importance of this tool to malaria campaigns in the Americas can be illustrated by the circumstances facing Peru's Ministry of Health (MINSA) clinics in the department of Loreto. It has been estimated that the total cost of treating malaria in Loreto in 1998 was $190 per individual case per year (in 1998 dollars). That cost included transportation of the patient to state clinics, treatment, medication, lost income, and the cost to the state of its free-treatment subsidy.[35]

TABLE 2

Efficacy of 2 repellents tested 3 to 6 hours after application during study B in Peru

| Treatment | | All mosquitoes Hours post application | | | | | | Anopheles darlingi Hours post application | | | | |
|---|---|---|---|---|---|---|---|---|---|---|---|---|
| | | 3 | 4 | 5 | 6 | Mean | 95% C.I. | 3 | 4 | 5 | 6 | Mean | 95% C.I. |
| 20% oil control | AM | 44.44 | 62.11 | 38.44 | 40.11 | 46.27 | 28.08-46.47 | 31.11 | 54.78 | 34.11 | 35.44 | 38.86 | 20.12-37.47 |
| | WM | 34.52 | 53.05 | 31.46 | 29.27 | 35.97$^a$ | | 22.10 | 44.60 | 23.05 | 24.79 | 27.50$^a$ | |
| | % P | — | — | — | — | — | | — | — | — | — | — | |
| PMD + LG | AM | 1.33 | 1.78 | 1.67 | 4.78 | 2.38 | 00.73-02.10 | 1.11 | 1.56 | 1.44 | 3.89 | 2.00 | 0.63-1.80 |
| Repellent | WM | 0.82 | 1.08 | 1.15 | 2.52 | 1.32$^b$ | | 0.66 | 0.93 | 1.05 | 2.17 | 1.14$^b$ | |
| | % P | 97.07 | 97.10 | 95.57 | 87.50 | 94.85 | | 96.43 | 97.16 | 95.77 | 89.03 | 94.85 | |
| 20% DEET | AM | 15.22 | 19.78 | 13.89 | 18.44 | 16.83 | 10.13-17.17 | 13.56 | 18.33 | 12.89 | 17.22 | 15.00 | 9.18-15.78 |
| | WM | 10.59 | 16.12 | 11.68 | 15.28 | 13.30$^c$ | | 9.59 | 14.96 | 10.59 | 13.59 | 12.07$^c$ | |
| | % P | 65.77 | 68.12 | 63.80 | 52.08 | 63.63 | | 56.43 | 66.53 | 62.21 | 51.41 | 61.40 | |

AM = arithmetic mean mosquito landings/hour
WM = William's mean mosquito landings/hour. Means followed by the same latter are not significantly different.
% P = percentage protection i.e.100 − ((mosquito landings on treatment ÷ mosquito landings on control) × 100)

Discussion

In both field trials, the PMD/LG repellents with fixatives showed excellent efficacy against a broad range of mosquito Adjusted to 2006 dollars, that's the equivalent of $235. However, the estimated annual cost for the repellent intervention (coverage for an adult male during 7-month transmission season at $0.047/day) is $10.00. That's 4.2% of the total cost of treatment (using MINSA clinics) today, so it may be an excellent candidate for incorporation into existing vector control strategies.

If such economies could be achieved in Peru, while substantially reducing the disease burden from malaria, this model might be applicable to other regions where early evening biting is problematic. Essentially, the Repelling Malaria model proposes: (1) that wherever the crepuscular feeding behavior of the most significant malaria vectors is already established, or where it may be shifting to early evening (from IRS and/or ITN use[36] which reduces host-availability later in the evening; or from a growing diversity of anophlines, including crepuscular species, which may result from land-use changes)[37], then (2) in remote areas where the human reservoir of disease is migratory;[38] it may be possible to achieve within one year a reduction of perhaps 30-60% in malaria, and this achievement could be realized by flooding these areas with a highly repellent skin lotion (efficacy 6 hrs at >95%) that is affordable and aromatically attractive to the indigenous poor. Importantly, under this model, in the larger more stable populations of towns and small cities where the API is generally lower and where access to repellents is facilitated at clinics, pharmacies and markets, malaria has the potential to subside even further.

A five-month Phase 3 study (with a PMD/LG repellent) that is currently being organized in the Peruvian Amazon, will soon provide an opportunity to measure the parameters of the proposed model, with 3750 subjects divided into three cohorts (Repellent Only, Repellent+ITNs, and No Intervention). This community-wide study will mark the first time that the effect of a Repellent Only intervention on parasitemia has been measured in a discrete population group. If the repellent's demonstrated capacity to effectively repel malaria vectors leads to a measurable reduction in the infection rate, then Puerta del Cielo, the non-profit foundation that's funding and directing the Phase 3 study, will begin distributing the repellent at cost to poor malaria endemic communities throughout the Peruvian Amazon.

Example 4

Evaluation of the Efficacy of the Formulation of Example 2

The efficacy of the one-phase formulation of example 2 was evaluated against a positive control (Walgreen's brand insect repellent containing 23% DEET) in a one m³ cube containing mosquitoes. The mosquito cube contained approximately 186 mosquitoes, having a median age of about 2 days post-emergence. Extrapolating from a sample size of 11 mosquitoes, it is estimated that the cube contained about 110 females.

The "test zone" consisted of a 4×25 cm (100 sq cm) band of forearm just above each wrist. Each band was measured and marked using a paper template. This area was bordered with strips of 3M Transpore first aid tape. This area was additionally isolated by wearing a pair of latex gloves with cuffs that overlapped the tape. "The control zone" consisted of an area of untreated skin on the lower forearm and wrist created by partially rolling up the cuff of the glove.

200 microliters of each repellent was applied with the side of a pipetman pipetter to the test zone to spread the repellent evenly over the entire marked area. The formulation of Example 2 was applied to the left arm, Walgreen's brand 23% DEET was applied to the right arm. After application, 10 minutes were allowed for drying prior to inserting the arms into the mosquito cube. Latex gloves were worn on each hand, with cuffs overlapping the lowermost band of tape.

A negative control (untreated skin) was evaluated before each repellent exposure by rolling down the cuff to expose about 4 cm of untreated skin below the band of tape. The number of landings and attempted probes on this area were counted over a period of 2 minutes. (Note: Many more landings and probes occurred on the latex gloves, and cotton cage sleeve than on the exposed skin, but these were not counted.) A landing was defined as a complete cessation of wing movement after tarsal contact with skin. A probe was defined as continued contact with skin accompanied by touching of the mouthparts to the skin. Mosquitoes were shaken off after a count was taken and the observations were repeated over a period of 2 minutes.

Some landings were accidental and appeared to involve mosquitoes becoming entangled in arm hair. Probes are a more robust indicator of non-repellency, but landings are useful because they tend to increase in frequency as a repellent is beginning to fail over time.

The results are shown below:

| Time | Hours | Left Arm -- Negative Control | | 23% DEET | | Right Arm -- Negative Control | | Formulation of Example 2 | |
| --- | --- | --- | --- | --- | --- | --- | --- | --- | --- |
| | | Land | Probe | Land | Probe | Land | Probe | Land | Probe |
| 920 | 0 | 20 | 16 | 1 | 0 | 13 | 10 | 0 | 0 |
| 1020 | 1 | 21 | 20 | 2 | 0 | 23 | 21 | 0 | 0 |
| 1120 | 2 | 35 | 34 | 0 | 0 | 16 | 14 | 0 | 0 |
| 1220 | 3 | 25 | 25 | 0 | 0 | 12 | 11 | 1 | 0 |
| 1320 | 4 | 19 | 16 | 1 | 0 | 20 | 16 | 0 | 0 |
| 1420 | 5 | 41 | 37 | 0 | 0 | 34 | 32 | 3 | 0 |
| 1520 | 6 | 40 | 36 | 2 | 0 | 27 | 24 | 1 | 0 |

REFERENCES

1. Hay S I, Guerra C A, Tatem A J, Noor A M, Snow R W, 2004. The global distribution and population at risk of malaria: past, present, and future. *Lancet Infect Dis* 4: 327-36.
2. WHO, 2005. World malaria report 2005 (WHO/HTM/MAL/2005.1102). Geneva: World Health Organization and UNICEF, http://www.rbm.who.int/wmr2005/html/1-2.htm.
3. WHO, 2002. The World health Report 2002: reducing risks, promoting healthy life. Geneva: World Health Organization.
4. Tadei W P, Dutary Thatcher B, 2000. Malaria vectors in the Brazilian amazon: *Anopheles* of the subgenus *Nyssorhynchus*. *Rev Inst Med Trap Sao Paulo* 42: 87-94.
5. Trung H D, Bartel W V, Sochantha T, Keokenchanh K, Briet O J, Coosemans M, 2005. Behavioural heterogeneity of *Anopheles* species in ecologically different localities in Southeast Asia: a challenge for vector control. *Trop Med Int Health* 10: 251-62.
6. Rubio-Palis Y, Curtis CF, 1992. Biting and resting behaviour of anophelines in western Venezuela and implications for control of malaria transmission. *Med Vet Entomol* 6: 325-34.
7. Benet A, Mai A, Bockarie F, Lagog M, Zimmerman P, Alpers M P, Reeder J C, Bockarie M J, 2004. Polymerase chain reaction diagnosis and the changing pattern of vector ecology and malaria transmission dynamics in papua new Guinea. *Am J Trop Med Hyg* 71: 277-84.
8. Harris A F, Matias-Arnez A, Hill N, 2006. Biting time of *Anopheles darlingi* in the Bolivian Amazon and implications for control of malaria. *Trans R Soc Trop Med Hyg* 100: 45-7.
9. Takken W, 2002. Do insecticide-treated bednets have an effect on malaria vectors? *Trop Med Int Health* 7: 1022-30.
10. Braimah N, Drakeley C, Kweka E, Mosha F, Helinski M, Pates H, Maxwell C, Massawe C, Kenward M G, Curtis C, 2005. Tests of bednet traps (Mbita traps) for monitoring mosquito populations and time of biting in Tanzania and possible impact of prolonged insecticide treated bednet use. *Int J Trop Insect Sci* 25: 208-13.
11. Kroeger A, Meyer R, Mancheno M, Gonzalez M, Pesse K, 1997. Operational aspects of bednet impregnation for commuity-based malaria control in Nacaragua, Equador, Peru and Colombia. *Trop Med Int Health* 2: 589-602.
12. Alexander N, Rodriguez M, Perez L, Caicedo J C, Cruz J, Prieto G, Arroyo J A, Cotacio M C, Suarez M, F DLH, Hall A J, 2005. Case-control study of mosquito nets against malaria in the Amazon region of Colombia. *Am J Trop Med Hyg* 73: 140-8.
13. Costantini C, Badolo A, Ilboudo-Sanogo E, 2004. Field evaluation of the efficacy and persistence of insect repellents DEET, IR3535, and KBR 3023 against *Anopheles gambiae* complex and other Afrotropical vector mosquitoes. *Trans R Soc Trop Med Hyg* 98: 644-52.
14. Hii JLK, Kanai, L., Foligela, A., Kan, K. P., Burkot, T. R. and Wirtz, R. A., 1993. Impact of permethrin-impregnated bednets compared with DDT house-spraying against malaria transmission by *Anopheles farauti* and *An. punctulatus* in the Solomon Islands. *Medical and Veterinary Entomology*, 333-338.
15. Rowland M, Downey G, Rab A, Freeman T, Mohammad N, Rehman H, Durrani N, Reyburn H, Curtis C, Lines J, Fayaz M, 2004. DEET mosquito repellent provides personal protection against malaria: a household randomized trial in an Afghan refugee camp in Pakistan. *Trop Med Int Health* 9: 335-42.
16. Hill N, Lenglet A, Arnez A M, Carneiro I, 2005. Clinical evaluation of combined use of ITNs and plant-based insect repellents to control malaria in Bolivia. London: Malaria Centre Report, London School of Hygiene and Tropical Medicine, 50-51 http://www.lshtm.ac.uk/malaria/annual-report/report20042005.pdf.
17. Prothero R M, 2001. Migration and Malaria Risk. *Health, Risk and Society* 3: 19-38.
18. Jackson S, Sleigh A C, Liu X L, 2002. Cost of malaria control in China: Henan's consolidation programme from community and government perspectives. *Bull World Health Organ* 80: 653-9.
19. Vosti S, 1990. Malaria among gold miners in Southern Para, Prazil: estimates of determinants and individual costs. *Soc Sci Med* 30: 1097-105.
20. Pang L W, Piovesan-Alves F, 2001. Economic advantage of a community-based malaria management programme in the Brazilian Amazon. *Am J Trop Med Hyg* 65: 883-6.
21. Trigg J K, 1996. Evaluation of a eucalyptus-based repellent against *Anopheles* spp. in Tanzania. *J Am Mosq Control Assoc* 12: 243-6.
22. Moore S J, Lenglet A, Hill N, 2002. Field evaluation of three plant-based insect repellents against malaria vectors in Vaca Diez Province, the Bolivian Amazon. *J Am Mosq Control Assoc* 18: 107-10.
23. Schreck C E, Leonhardt B A, 1991. Efficacy assessment of Quwenling, a mosquito repellent from China. *J Am Mosq Control Assoc* 7: 433-6.
24. Sears R, 1996. An ethnobotanical survey of insect repellents in Brazil. *Tropical Resources Institiute Working Pages*. New Haven.
25. Rutledge L C, Gupta R K, Mehr Z A, Buescher M D, Reifenrath W G, 1996. Evaluation of controlled-release mosquito repellent formulations. *J Am Mosq Control Assoc* 12: 39-44.
26. Curtis C F, Lines J D, Ijumba J, Callaghan A, Hill N, Karimazad M A, 1987. The relative efficacy of repellents against mosquito vectors of disease. *Medical and Veterinary Entomology* 1: 109-19.
27. de Jong R, Knols B G J, 1995. Selection of biting sites on man by two malaria mosquito species. *Experientia* 51: 80-4.
28. Shirai O T, Tsuda T, Kitagawa S, Naitoh K, Seki K, K. K, Morohashi M, 2002. Alcohol ingestion stimulates mosquito attraction. *J Am Mosq Control Assoc* 18: 91-6.
29. Gillies M T, Wilkes T J, 1970. Range of attraction of single baits for some West-African mosquitoes. *Bulletin of Entomological Research* 60: 225-235.
30. WHO, 2005. *International travel and health*. Geneva: World Health Organisation.
31. Barnard D R, Bernier U R, Posey K H, Xue R D, 2002. Repellency of IR3535, KBR3023, para-menthane-3,8-diol, and deet to black salt marsh mosquitoes (*Diptera: Culicidae*) in the Everglades National Park. *J Med Entomol* 39: 895-9.
32. Harris A, 2003. The potential for plant-based insect repellents to play a significant role in the control of vector-borne disease. *ITD MSc Thesis*. London: London School of Hygiene and Tropical Medicine.
33. Worrall E, Basu S, Hanson K, 2005. Is malaria a disease of poverty? A review of the literature. *Tropical Medicine and International Health* 10: 1047-1059.
34. Kroeger A, Gerhardus A, Kruger G, Mancheno M, Pesse K, 1997. The contribution of repellent soap to malaria control. *Am J Trop Med Hyg* 56: 580-4.
35. MINSA/USAID, 2000. Impacto Econamico de La Malaria En El Perú. Lima, Perú: Ministerio de Salud.
36. Charlwood J D, 1996. Biological variation in *Anopheles darlingi* (Root). *Memorias de Instituti Oswaldo Cruz* 91: 391-8.
37. Povoa M M, Conn J E, Schlichting C D, Amaral J C, Segura M N, Da Silva A N, Dos Santos C C, Lacerda R N, De Souza R T, Galiza D, Santa Rosa E P, Wirtz R A, 2003. Malaria vectors, epidemiology, and the re-emergence of *Anopheles darlingi* in Belem, Para, Brazil. *J Med Entomol* 40: 379-86.
38. Conn J E, Wilkerson R C, Segura M N, de Souza R T, Schlichting C D, Wirtz R A, Povoa M M, 2002. Emergence of a new neotropical malaria vector facilitated by human migration and changes in land use. *Am J Trop Med Hyg* 66: 18-22.
39. Rowland M, Freeman T, Downey G, Hadi A, Saeed M, 2004a. DEET mosquito repellent sold through social marketing provides personal protection against malaria in an area of all-night mosquito biting and partial coverage of insecticide-treated nets: a case-control study of effectiveness. *Trop Med Int Health* 9: 343-50.

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

The invention claimed is:

1. An insect repellent composition comprising
   (a) lemongrass oil;
   (b) less than 21 weight % of p-menthane-3,8 diol; and
   (c) vanillin, and
   wherein the amount of lemongrass oil and p-menthane-3,8 diol is from about 10 weight % to about 35 weight %, based on the total weight of the insect repellent composition.

2. The composition of claim 1, further comprising at least one of mineral oil, ethanol, dipropylene glycol, isoparaffinic hydrocarbon, and isononyl acetate.

3. An insect repellent composition comprising mineral oil, ethanol, p-menthane-3,8 diol, dipropylene glycol, lemongrass oil and vanillin, wherein the composition comprises less than 21 weight % p-menthane-3,8 diol, wherein the amount of lemongrass oil and p-menthane-3,8 diol is from about 10 weight % to about 35 weight %, based on the total weight of the insect repellent composition.

4. An insect repellent composition comprising mineral oil, isoparaffinic hydrocarbon, p- menthane,3,8 diol, isononly acetate, lemongrass oil and vanillin, wherein the composition comprises less than 21 weight % p-menthane-3,8 diol, wherein the amount of lemongrass oil and p-menthane-3,8 diol is from about 10 weight % to about 35 weight %, based on the total weight of the insect repellent composition.

5. The insect repellent composition of claim 1, wherein the formulation is a one-phase formulation.

6. The insect repellent composition of claim 1, wherein the formulation is a two-phase formulation.

7. A method of repelling insects comprising topically applying the composition of claim 1 to the skin of an animal.

8. A method of preventing malaria comprising topically administering the composition of claim 1 to the skin of an animal.

9. The method of claim 8, wherein the animal is a human.

10. The insect repellent composition of claim 1, wherein the formulation is applied to a surface with a delivery vehicle.

11. The insect repellent composition of claim 10, wherein the delivery vehicle is water, an aerosol, spray, gel or lotion.

12. The insect repellent composition of claim 11, wherein the delivery vehicle is a gel.

13. The insect repellent composition of claim 12, wherein the gel contains a xanthan gum gelling agent.

14. A method of repelling insects comprising topically applying the composition of claim 3 to the skin of a human.

15. A method of repelling insects comprising topically applying the composition of claim 4 to the skin of a human.

* * * * *